US009763710B2

(12) United States Patent
Orsak et al.

(10) Patent No.: US 9,763,710 B2
(45) Date of Patent: Sep. 19, 2017

(54) MODULAR PROXIMAL FEMORAL OSTEOTOMY BLADE-PLATE ASSEMBLY AND RELATED FIXATION METHOD

(71) Applicant: PEGA MEDICAL, INC., Lavel (CA)

(72) Inventors: James Orsak, Laval (CA); Shawn Standard, Laval (CA); Fady Rayes, Laval (CA); Ariel Dujovne, Laval (CA)

(73) Assignee: Pega Medical, Inc., Lavel (CA)

( * ) Notice: Subject to any disclaimer, the term of this patent is extended or adjusted under 35 U.S.C. 154(b) by 455 days.

(21) Appl. No.: 14/480,077

(22) Filed: Sep. 8, 2014

(65) Prior Publication Data

US 2016/0066968 A1 Mar. 10, 2016

(51) Int. Cl.
*A61B 17/74* (2006.01)
*A61B 17/80* (2006.01)

(52) U.S. Cl.
CPC ............ *A61B 17/746* (2013.01); *A61B 17/74* (2013.01); *A61B 17/742* (2013.01); *A61B 17/8042* (2013.01)

(58) Field of Classification Search
CPC ..... A61B 17/74; A61B 17/742; A61B 17/746; A61B 17/809; A61B 17/8095
See application file for complete search history.

(56) References Cited

U.S. PATENT DOCUMENTS 6,183,475 B1 * 2/2001 Lester ................ A61B 17/8095
606/281
8,579,945 B2 * 11/2013 Appenzeller ...... A61B 17/8061
606/281

* cited by examiner

*Primary Examiner* — Andrew Yang
(74) *Attorney, Agent, or Firm* — Polsinelli PC (57) ABSTRACT

A blade-plate assembly for performing an osteotomy procedure is disclosed. The blade-plate assembly may include a modular blade component configured to be coupled to either a Varus plate component or a Valgus plate component when performing the osteotomy procedure. In some embodiments, the modular blade component includes a support portion and a blade portion that extends outwardly in perpendicular relation to the support portion. The blade portion defines a channel configured to permit passage of a guide wire when performing the osteotomy procedure.

22 Claims, 9 Drawing Sheets

MODULAR PROXIMAL FEMORAL OSTEOTOMY BLADE-PLATE ASSEMBLY AND RELATED FIXATION METHOD

FIELD

This document generally relates to systems and methods for the fixation of osteotomies and fractures to the proximal femur, and in particular to a modular proximal femoral osteotomy blade-plate assembly having a modular blade component adaptable to couple with different types of plate components.

BACKGROUND

Proximal femoral osteotomy (PFO) is a widely performed reconstructive surgery in children with neurologic hips. Asymmetric muscle forces produced across the hip are responsible for the development of hip deformities, such as coxa valga, persistent femoral anteversion, acetabular dysplasia, windswept deformity, and pelvic obliquity. Incidence of these hip deformities varies with the severity of the disease, and may lead to hip dislocation in more than 75% of severe spastic quadriplegic patients as reported in Khouri et at. Entitled "Proximal Femoral Osteotomy in Neurologic Pediatric hips Using the Locking Compression Plate (J Pediatric Orthopedic 2010; 30:825-831.

Other deformities of the proximal hip include developmental coxa vara and hinge abduction. Valgus subtrochanteric osteotomy is the current gold standard for treatment of coxa vara, while treatment of hinge abduction is also done through valgus osteotomy in children with severely involved Legg-Calvé-Perthes disease.

PFO has been shown to have a significant role in correcting these acquired deformities. Many implants have been used for the fixation of PFOs. With the development of the association for osteosynthesis instrumentation, the single-piece 90 degrees fixed-angle blade plate has come to be widely used. Other pediatric instrumentation have also been developed using a two-piece sliding hip screw (Richards intermediate hip screw) with the insertion of the sliding screw in the center of the femoral neck. Later devices consist of a screw-plate implant or blade-plate implant with insertion of an "antirotation screw" for engaging the proximal fragment and providing enhanced antirotation fixation. These types of devices have shown more successful fixation; however, discomfort, bursitis, and even skin breakdown with the exposure of the underlying plate can occur due to the bulkiness of these types of implants. Position change of the proximal fragment and loss of fixation have also been observed in some osteoporotic patients.

As such, there is a need for a blade-plate device that simplifies the surgical technique via a chisel-free modular system and creates a biomechanically correct lateralization or medicalization of the femoral shaft depending on the type of osteotomy being performed.

SUMMARY

In an embodiment, a blade-plate assembly is provided that is modular in construction and configured for stable fixation of proximal femoral osteotomies and fractures in pediatric patients.

In some embodiments, the blade-plate assembly may include a modular blade component configured to be secured to a Varus or Valgus plate component. The modular blade component includes a support portion attached to the plate component and a blade portion that extends from the support portion for implantation within the bone tissue of an individual, for example in the femoral neck and head, while the plate component is anchored to the shaft of the femur of the individual using fastening members.

In some embodiments, the modular blade component includes a cannulated blade portion forming a channel configured to allow a guide wire to extend through the modular blade component to aid in implantation.

In one method of implantation, a modular blade component is implanted within the bone tissue independent of the plate component. Once the modular blade component is implanted and the osteotomy performed, the plate component is attached to the modular blade component and then anchored to the shaft of the femur using fastening members to achieve the desired neck-to-shaft angle.

Additional objectives, advantages and novel features will be set forth in the description which follows or will become apparent to those skilled in the art upon examination of the drawings and detailed description which follows.

Corresponding reference characters indicate corresponding elements among the view of the drawings. The headings used in the figures do not limit the scope of the claims.

DETAILED DESCRIPTION

Embodiments of an osteotomy blade-plate assembly having a modular blade component configured to be coupled to either a Varus plate component or a Valgus plate component and which is first implanted within the bone tissue independent of the plate component are disclosed. Once the modular blade component is implanted within the proximal femoral segment of an individual and an osteotomy performed, the Varus plate component or Valgus plate component is attached to the modular blade component and then anchored to the shaft of the femur using fastening members to achieve the desired neck-to-shaft angle. In reference to the drawings, embodiments of a Varus blade-plate assembly and a Valgus blade-plate assembly are illustrated and generally indicated as 100 and 200, respectively, in FIGS. 1-37.

Figure 1:
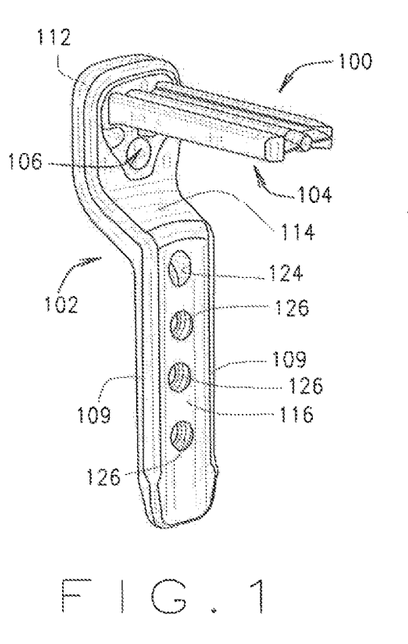
FIG. 1 is a perspective view of a first embodiment of a blade-plate assembly showing a modular blade component coupled to a Varus plate component.
Figure 2:
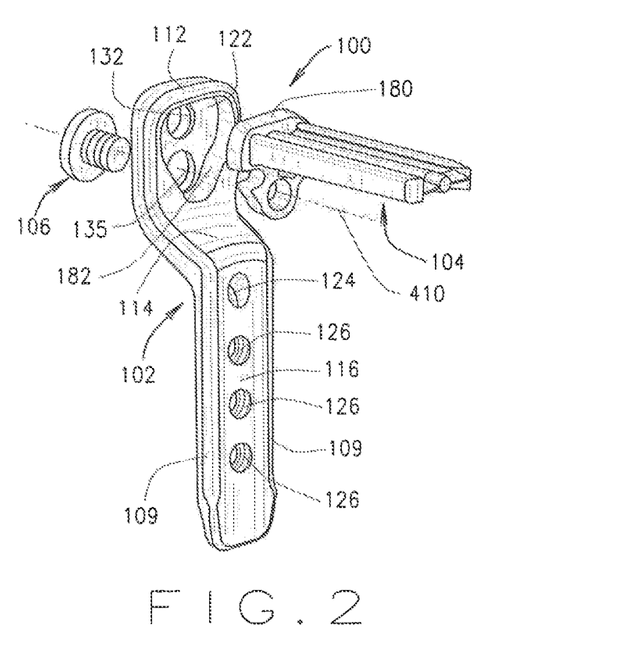
FIG. 2 is an exploded view of the blade-plate assembly of FIG. 1.
Figure 3:
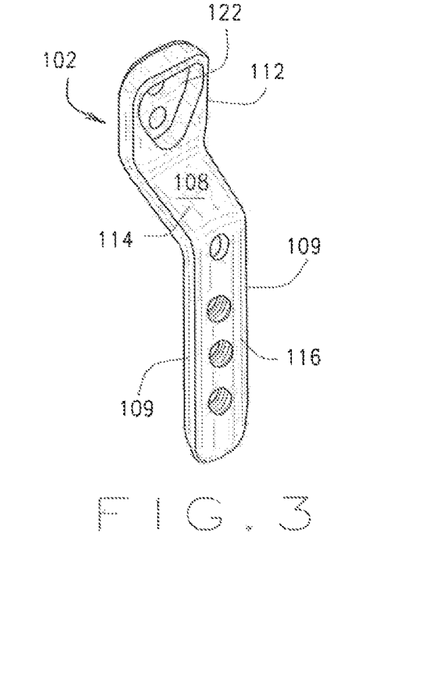
FIG. 3 is a perspective view of the Varus plate component of FIG. 1.
Figures 19, 21:
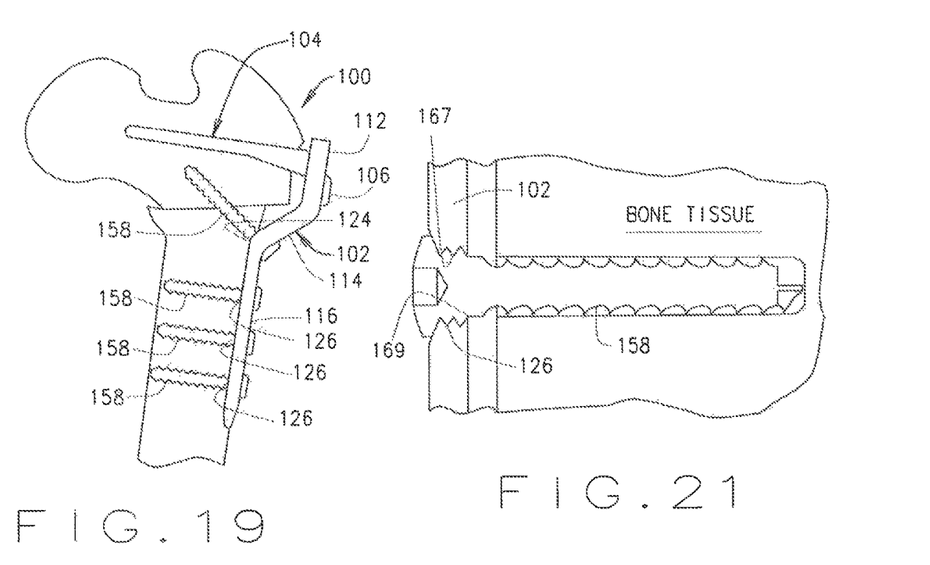
FIG. 19 is a side view showing the blade-plate assembly of FIG. 1 secured to bone tissue.
FIG. 21 is a cross-sectional view of a fastening member secured to the plate assembly of FIG. 1.

Referring to FIGS. 1-21, an embodiment of a Varus blade-plate assembly, designated 100, is illustrated. As shown in FIGS. 1 and 2, the Varus blade-plate assembly 100 may include a Varus plate component 102 configured to be coupled to a modular blade component 104 using a connector 106 that secures the Varus plate component 102 with the modular blade component 104 once implantation of the modular blade component 104 is completed and prior to the osteotomy being performed. As shown in FIG. 19, in one method of implantation of the Varus blade-plate assembly 100 the modular blade component 104 is implanted into the proximal femoral segment of an individual and then the Varus plate component 102 is later coupled to the modular blade component 104 using the connector 106. The Varus plate component 102 is then engaged to the distal femoral segment of the individual using fastening members 158 inserted through openings 126 of the Varus plate component 102 and into the bone tissue as shall be discussed in greater detail below.

Figure 4:
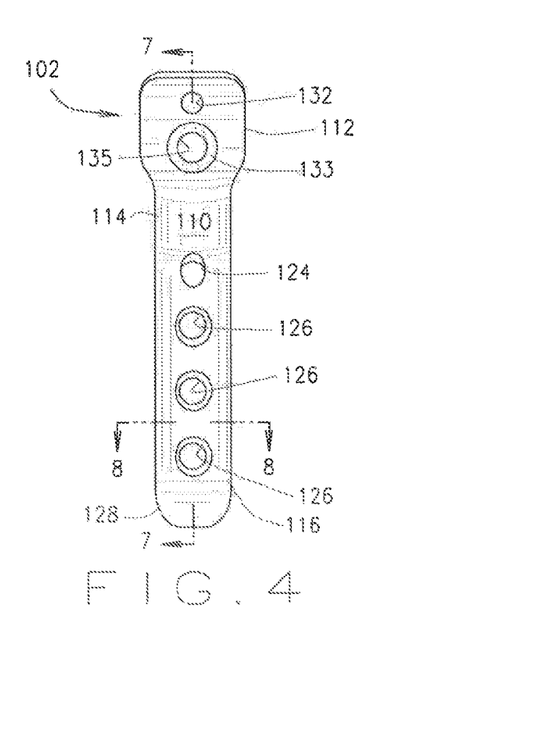
FIG. 4 is a rear view of the Varus plate component of FIG. 1.
Figures 5, 6, 7, 8:
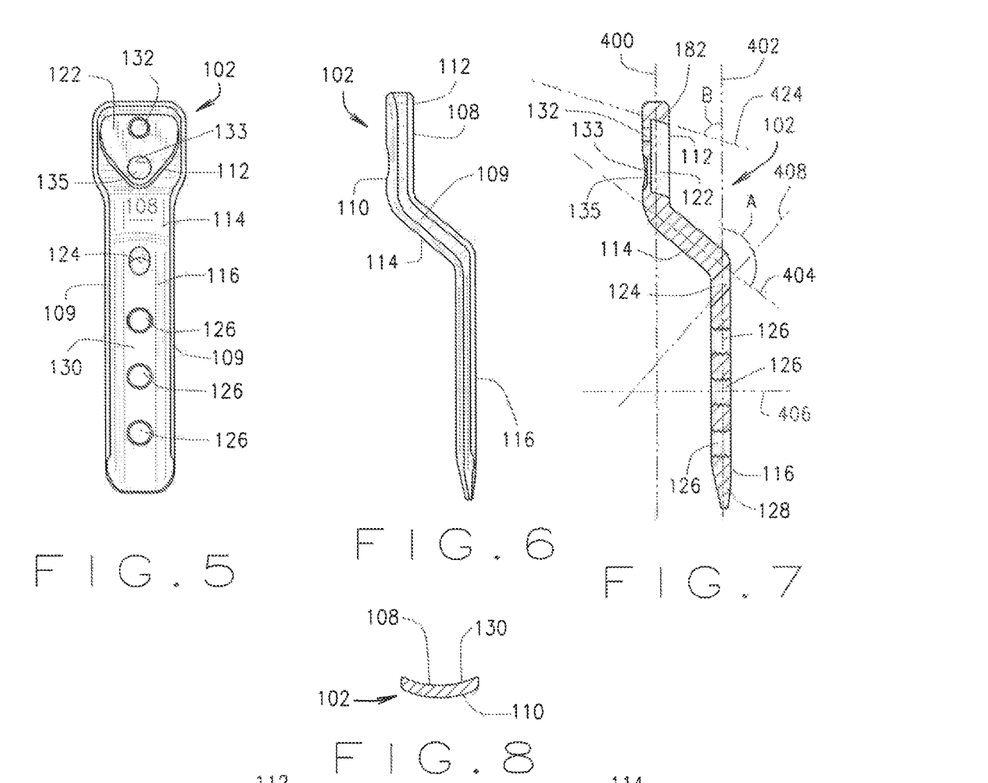
FIG. 5 is a front view of the Varus plate component of FIG. 1.
FIG. 6 is a side view of the Varus plate component of FIG. 1.
FIG. 7 is a cross-sectional view of the Varus plate component taken along line 7-7 of FIG. 4.
FIG. 8 is a cross-sectional view of the Varus plate component taken along line 8-8 of FIG. 4.
Figure 9:
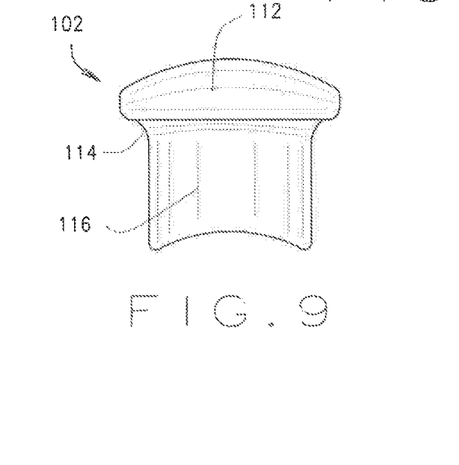
FIG. 9 is a top view of the Varus plate component of FIG. 1.
Figure 10:
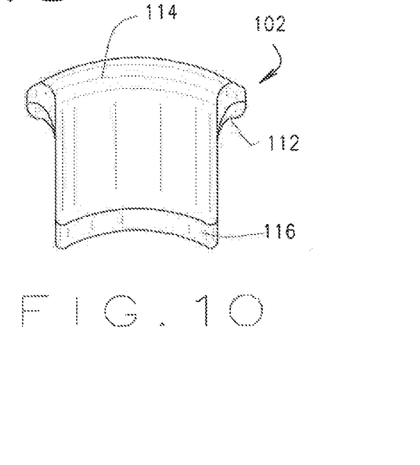
FIG. 10 is a bottom view of the Varus plate component of FIG. 1.
Figure 11:
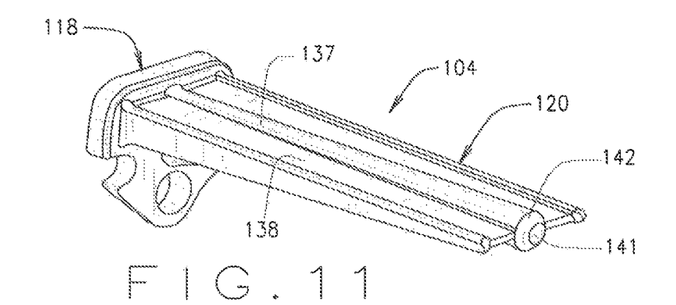
FIG. 11 is a perspective view of the modular blade component used with the first and second embodiments of the blade-plate assembly of FIGS. 1 and 22.

As shown in FIGS. 3-10, the Varus plate component 102 defines an anterior surface 108, a side surface 109, and a posterior surface 110 that collectively form a proximal portion 112, a transition portion 114 and a distal portion 116 of the Varus plate component 102. Referring to FIG. 7, in some embodiments the proximal portion 112 is aligned along a longitudinal axis 400, while distal portion 116 is aligned in parallel orientation along a longitudinal axis 402; however, in other embodiments the proximal portion 112 may be oriented in non-parallel relation relative to the distal portion 116 to form various angles (e.g., 100 degrees, 110 degrees) between longitudinal axes 400 and 402. As further shown, the transition portion 114 is aligned along an axis 404 which is oriented at an angle relative to the proximal portion 112 and distal portion 116, respectively. For example, axis 404 may be oriented at an angle A relative to longitudinal axis 402.

Referring to FIGS. 2, 3, 5 and 7, the proximal portion 112 of the Varus plate component 102 defines a first recess 122 configured to engage the modular blade component (FIGS. 1, 2 and 12-15) when assembling the Varus blade-plate assembly 100. As shown in FIGS. 4, 5 and 7, the proximal portion 112 defines a clearance hole 132 and a second recess 133 formed along the posterior surface 110 that communicate with the larger first recess 122 formed along the anterior surface 108. The clearance hole 132 provides a conduit for permitting communication with the modular blade component 104 when the Varus plate component 102 is coupled to the modular plate component 104 to permit insertion of a guide wire (not shown) through the modular blade component 104. Referring to FIGS. 1, 2, 4, 5 and 7, the second recess 133 defines a recess opening 135 configured to receive a connector 106 that secures the Varus plate component 102 to the modular blade component 104 when Varus plate component 102 and the modular blade component 104 are aligned along axis 410 as illustrated in FIG. 2.

As noted above, the distal portion 116 of the Varus plate component 102 defines a plurality of openings 126 aligned along the longitudinal axis 402 defined by the distal portion 116 and oriented along a latitudinal axis 406 that is in perpendicular relation relative to the longitudinal axis 402. As shown, each of the openings 126 is configured to receive a respective fastening member 158 (FIGS. 19, 33 and 34) that secures the Varus plate component 102 to the bone tissue, such as the shaft of the femur of an individual. The distal portion 116 may further define a seating 124 with an opening aligned along an axis 408 at an angle relative to the plurality of openings 126 aligned along latitudinal axis 406. The angled alignment of the seating 124 allows a fastening member 158 to be inserted into the bone tissue at an angle different than the respective fastening members 158 inserted through openings 126 as illustrated in FIG. 19.

Referring to FIGS. 5 and 8, in some embodiments the anterior surface 108 of the distal portion 116 may define a curved surface 130, which is configured to comport to the curvature of the bone tissue when the Varus plate component 102 is secured to the bone. In some embodiments, the distal portion 116 may define a tapered end portion 128 that communicates with the curved surface 130 as shown in FIGS. 4 and 7.

Figure 12:
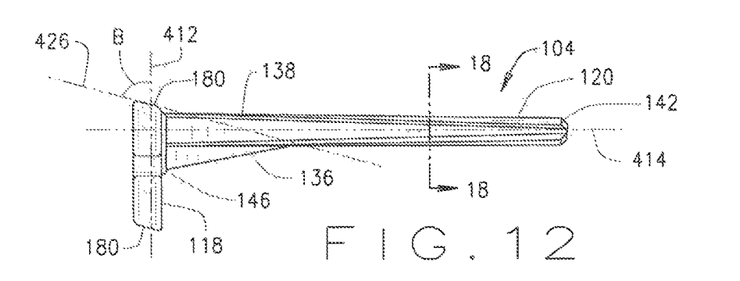
FIG. 12 is a side view of the modular blade component of FIG. 11.

As shown in FIGS. 11-18, the modular blade component 104 provides a modular component configured to couple with either the Varus plate component 102 (FIGS. 1-10) or the Valgus plate component 202 (FIGS. 22-32), thereby allowing the modular plate component 104 to be coupled to both embodiments of the blade-plate assembly 100 and 200. Referring to FIGS. 11-18, the modular blade component 104 includes a support portion 118 and a cannulated blade portion 120. The support portion 118 of the modular blade component 104 is configured to be seated within the first recess 122 (FIG. 2) when coupling the modular plate component 104 to the Varus plate component 102 during assembly of the Varus blade-plate assembly 100. As shown in FIG. 12, cannulated blade portion 120 extends axially from the support portion 118 along longitudinal axis 414 in perpendicular relation relative to the support portion 118 oriented along latitudinal axis 412.

Figure 13:
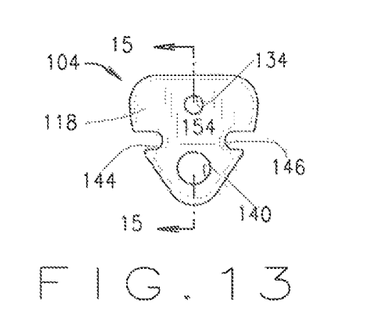
FIG. 13 is a rear view of the modular blade component of FIG. 11.
Figure 14:
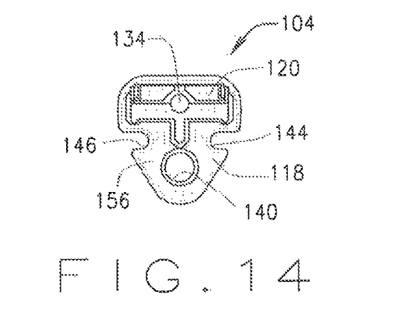
FIG. 14 is a front view of the modular blade component of FIG. 11.
Figures 15, 18:
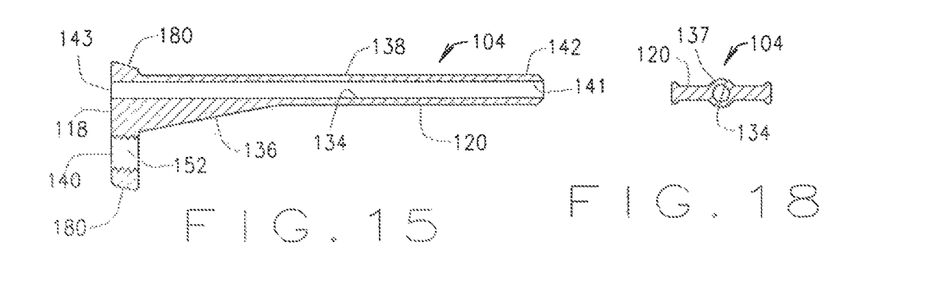
FIG. 15 is a cross-sectional view of the modular blade component taken along line 15-15 of FIG. 13.
FIG. 18 is a cross-sectional view of the modular blade component taken along line 18-18 of FIG. 12.

Referring to FIGS. 13 and 14, the support portion 118 defines a rear surface 154 and an opposite front surface 156 that collectively define a connector aperture 140 configured to engage the connector 106 (FIG. 2) when coupling the modular blade component 104 to the Varus plate component 102. As shown in FIG. 15, the connector aperture 140 defines internal threads 152 configured to be coupled to the external threads 174 (FIG. 35) of connector 106. Referring back to FIGS. 13 and 14, in some embodiments, the support portion 118 forms opposing first and second notches 144 and 146 configured to engage a drive tool (not shown) for implanting the modular blade component 104 into bone tissue (FIG. 19).

Figure 16:
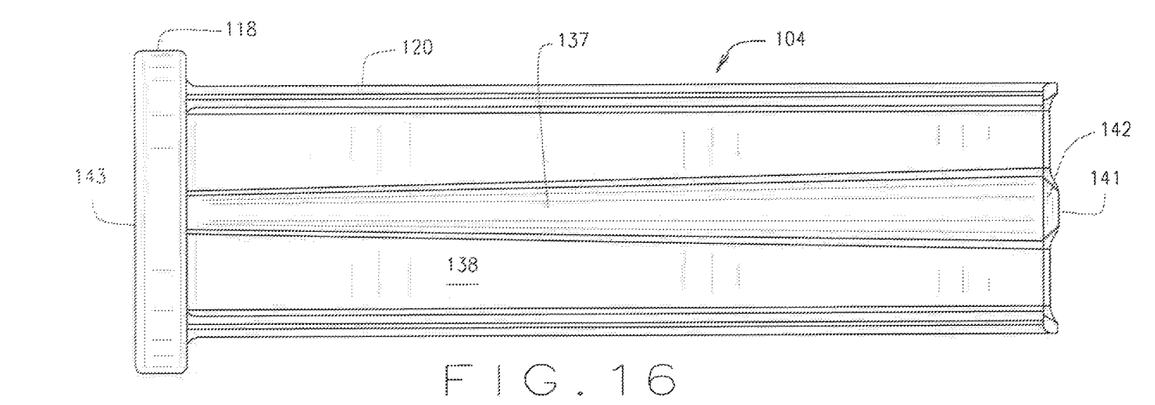
FIG. 16 is a top view of the modular blade component of FIG. 11.
Figure 17:
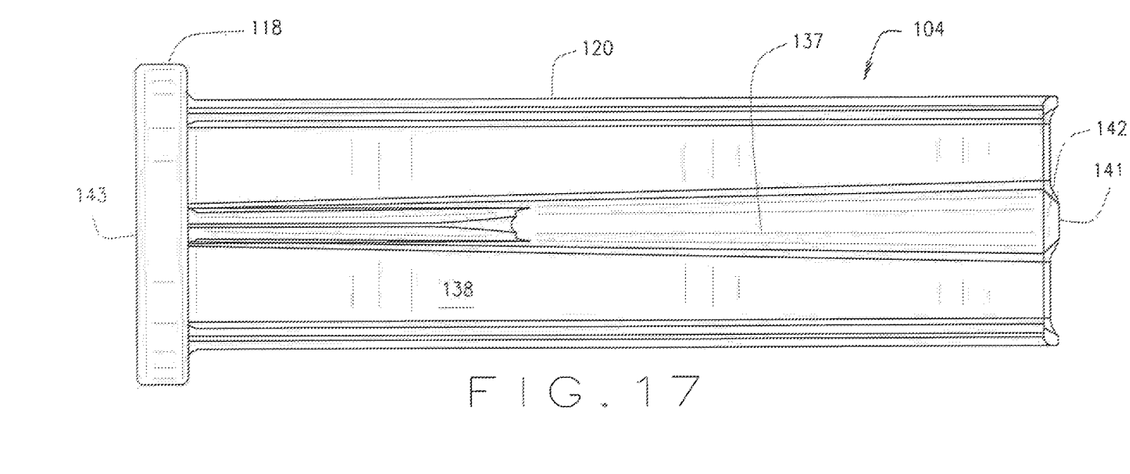
FIG. 17 is a bottom view of the modular blade component of FIG. 11.

Referring to FIGS. 13-15, the blade portion 120 and support portion 118 collectively define an axial channel 134 that extends along longitudinal axis 414 (FIG. 12) and is configured to allow passage of a guide wire (not shown) through the blade portion 120. As shown in FIGS. 12 and 15, the blade portion 120 defines a beam 138 with a keel 136 formed underneath the beam 138 that provides structural support to the blade portion 120. In addition, as shown in FIGS. 11, 12, and 15-18, the blade portion 120 includes a central conduit 137 that forms a first opening 141 at the blade tip 142 of blade portion 120 and an opposite second opening 143 formed at the support portion 118 that communicate with the opposite ends of the axial channel 134 as illustrated in FIG. 15. Referring to FIGS. 12, 16 and 17, in various embodiments the beam 138 of the modular blade component 104 may have a variety of lengths and thicknesses that form a continuous or tapered profile.

Referring to FIGS. 2, 7 and 12, the recess 122 of the Varus plate component 102 and the support portion 118 of the modular blade component 104 collectively form a self-retention feature that allows the support portion 118 to be coupled and retained within the recess 122 by virtue of complementary angled surfaces that establish an angled mating engagement with each other. In particular, the support portion 118 defines a first angled mating surface 180 that is configured to mate with a complementary second angled mating surface 182 defined along the peripheral area of the recess 122 of the Varus plate component 102. As shown in FIG. 7, the second angled mating surface 182 of the recess 122 is aligned along an axis 424 that forms an angle B relative to the longitudinal axis 402 of the Varus plate component 102. Similarly, as illustrated in FIG. 12, the first angled mating surface 180 of the support portion 118 is aligned along an axis 426 that defines the same angle B relative to the longitudinal axis 412 of the support portion 118 such that the first and second angled mating surfaces 180 and 182 form complementary angled mating surfaces regardless of the respective angle defined by both the first and second angled mating surfaces 180 and 182.

Figure 20:
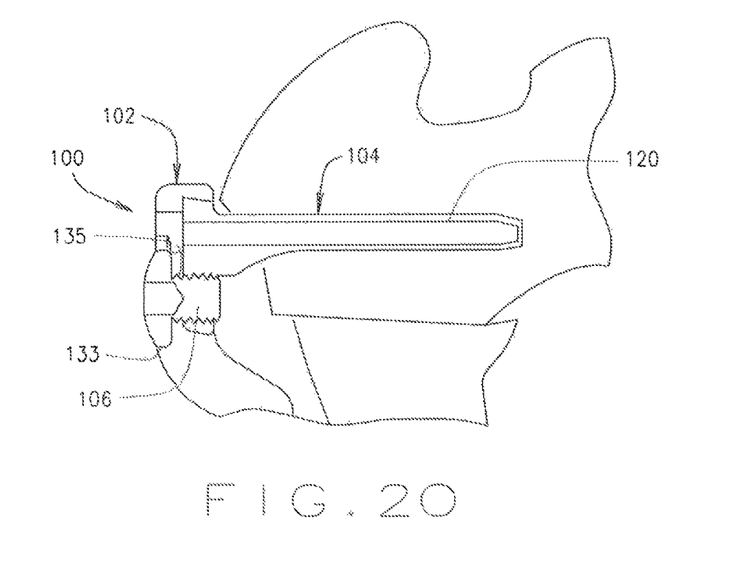
FIG. 20 is a cross-sectional view of the blade-plate assembly of FIG. 1 implanted within bone tissue.

Referring to FIG. 20, a cross-sectional view of the Varus blade-plate assembly 100 shows the modular blade component 104 coupled to the Varus plate component 102 and blade portion 120 implanted in the bone tissue. In addition, the connector 106 is shown inserted through the recess opening 135 of the second recess 133 such that the connector 106 is coupled to the Varus plate component 102 and the modular blade component 104 after the modular plate component 104 has been implanted in the bone tissue.

Referring to FIG. 21, a cross-sectional view of the Varus plate component 102 illustrates the engagement of the fastening member 158 through the Varus plate component 102 and into bone tissue. As shown, the fastening member 158 is configured to be received through the opening 126 of the Varus plate component 102 such that the transition section 167 of the fastening member 158 mates with the internal threads 169 of opening 126.

Figure 22:
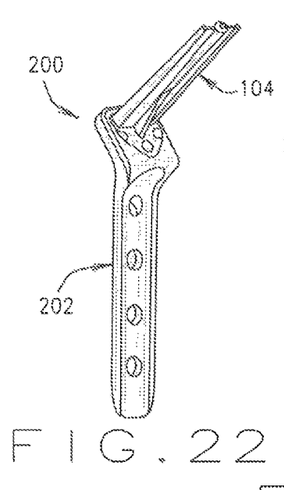
FIG. 22 is a perspective view of a second embodiment of a blade-plate assembly showing the modular blade component coupled to a Valgus plate component.
Figure 23:
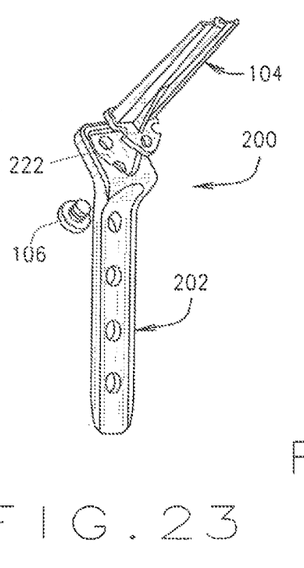
FIG. 23 is an exploded view of the blade-plate assembly of FIG. 22.
Figure 32:
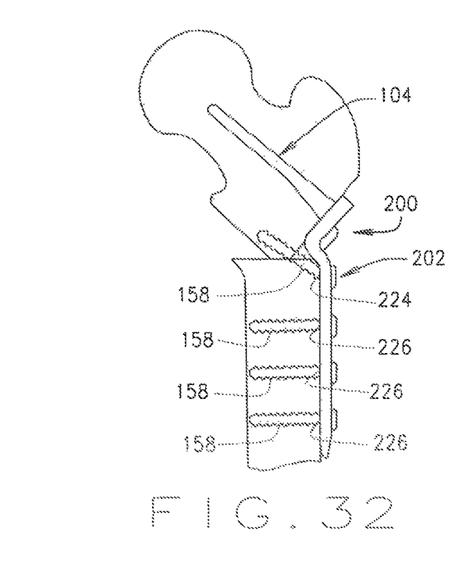
FIG. 32 is a side view showing the blade-plate assembly of FIG. 22 secured to bone tissue.

Referring to FIGS. 22-32, an embodiment of a Valgus blade-plate assembly, designated 200, is illustrated. As shown in FIGS. 22 and 23, the Valgus blade-plate assembly 200 may include a Valgus plate component 202 configured to be coupled to the modular blade component 104 as described above using the connector 106 to secure the Valgus plate component 202 with the modular blade component 104 once implantation of the modular blade component 204 is completed and after the osteotomy has been performed. As shown in FIG. 32, in one method of using the Valgus blade-plate assembly 200 the modular blade component 104 is implanted into the proximal femoral segment of an individual and then the Valgus plate component 202 is later coupled to the modular blade component 104. Once the modular blade component 102 is coupled to the Valgus plate component 202, the Valgus plate component 202 is engaged to the distal femoral segment of an individual through fastening members 158 inserted through the openings 226 of the Valgus plate component 202 and into the bone tissue as shall be discussed in greater detail below.

Figure 28:
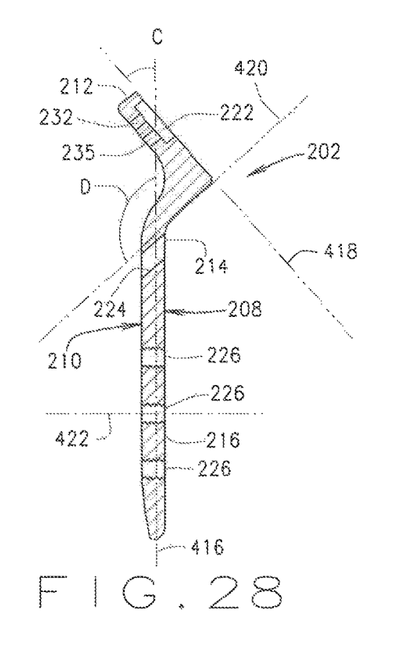
FIG. 28 is a cross-sectional view of the Valgus plate component taken along line 28-28 of FIG. 25.

As shown in FIGS. 24-31, the Valgus plate component 202 defines an anterior surface 208, a side surface 209, and a posterior surface 210 that collectively form a proximal portion 212, a transition portion 214 and a distal portion 216 of the Valgus plate component 202. Referring to FIG. 28, in some embodiments the distal portion 216 of the Valgus plate component 202 is aligned along a longitudinal axis 416, while proximal portion 212 is aligned along an axis 418 which is oriented at an angle C relative to longitudinal axis 416. As further shown, the transition portion 214 is aligned along an axis 420 which is oriented at an angle D relative to the longitudinal axis 416 of the distal portion 216.

Referring to FIGS. 23, 24, 26, 28 and 31, the proximal portion 212 of the Valgus plate component 202 defines a first recess 222 configured to engage the modular blade component 104 (FIGS. 12-15, 22 and 23) when assembling the Valgus blade-plate assembly 200. As shown in FIGS. 24, 25, 26 and 31, the proximal portion 212 defines a clearance hole 232 and a second recess 233 that communicate with the first recess 222. The clearance hole 232 provides a conduit for permitting communication with the support portion 118 of the modular blade component 104 when the Valgus plate component 202 is coupled to the modular plate component 104 to permit insertion of a guide wire (not shown) through the modular blade component 104. As shown in FIGS. 25, 26, 28 and 31, the second recess 233 defines a recess opening 235 configured to receive the connector 106 that secures the Valgus plate component 202 to the modular blade component 104 when assembling the Valgus blade-plate assembly 200.

Referring to FIG. 28 as noted above, the distal portion 216 defines a plurality of openings 226 (FIGS. 25, 26, 28 and 32)

aligned along the latitudinal axis 422 which are configured to receive a respective fastening member 158 therein (FIGS. 32, 33 and 34) that secures the Valgus plate component 202 to the bone tissue, such as the shaft of the femur of an individual. The distal portion 216 may further define a seating 224 with an opening substantially aligned in parallel alignment along axis 420. As shown in FIG. 32, the angled alignment of the seating 224 allows a fastening member 158 to be inserted into the bone tissue at an angle different than the respective fastening members 158 inserted through openings 226 as illustrated in FIG. 32.

Figure 24:
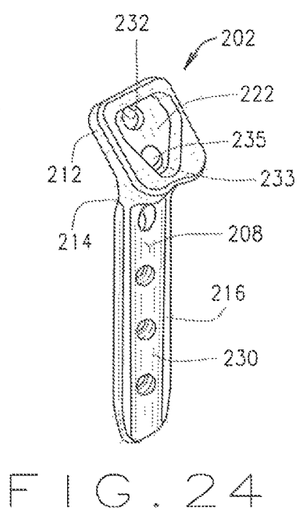
FIG. 24 is a perspective view of the Valgus plate component of FIG. 22.
Figures 25, 26, 27:
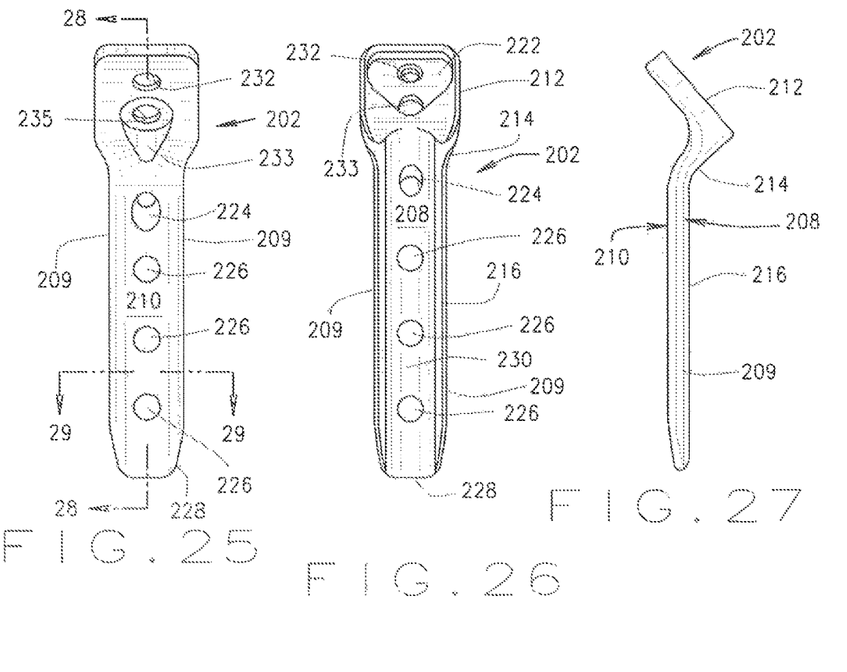
FIG. 25 is a rear view of the Valgus plate component of FIG. 22.
FIG. 26 is a front view of the Valgus plate component of FIG. 22.
FIG. 27 is a side view of the Valgus plate component of FIG. 22.
Figure 29:
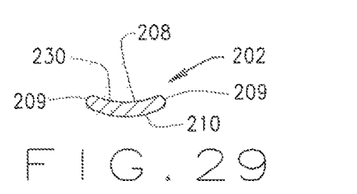
FIG. 29 is a cross-sectional view of the Valgus plate component taken along line 28-28 of FIG. 25.
Figure 30:
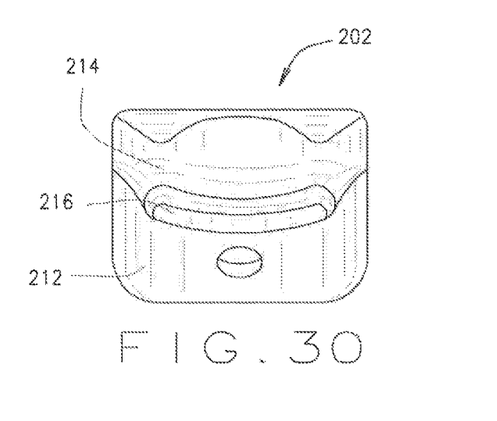
FIG. 30 is a bottom view of the Valgus plate component of FIG. 22.
Figure 31:
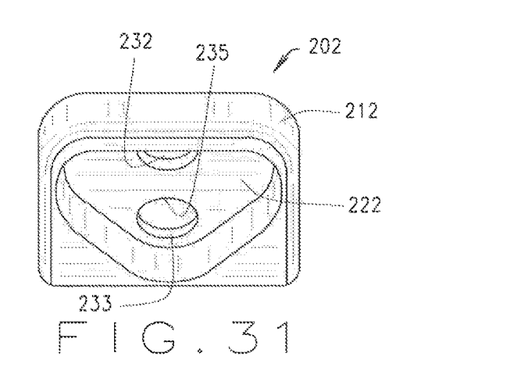
FIG. 31 is a top view of the Valgus plate component of FIG. 22.

Referring to FIGS. 24, 26 and 29, similar to the distal portion 116, in some embodiments the anterior surface 208 of the distal portion 216 for the Valgus plate component 202 may define a curved surface 230, which is configured to comport to the curvature of the bone tissue when the Valgus plate component 202 is secured to the bone. As shown in FIGS. 25 and 26, in some embodiments, the distal portion 216 may define a tapered end portion 228 that communicates with the curved surface 230.

Figure 33:
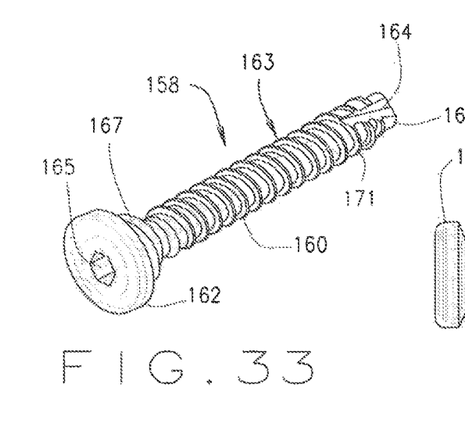
FIG. 33 is a perspective view of a cortical screw.
Figure 34:
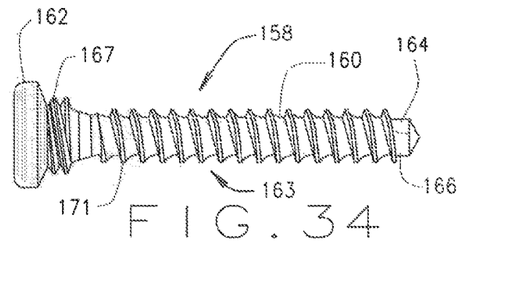
FIG. 34 is a side view of the cortical screw of FIG. 33.

Referring to FIGS. 33 and 34, the fastening member 158 used to secure the Varus blade-plate assembly 100 and the Valgus blade-plate assembly 200 to bone tissue is illustrated. In one embodiment, the fastening member 158 may include a shaft portion 160 that extends axially from a head portion 162. In some embodiments, the shaft portion 160 defines a threaded feature 163 defining a plurality of external threads 171 formed between a transition section 167 and a self-tapping feature 164 defined at the free end of the shaft portion 160.

As shown in FIG. 33, in some embodiments the head portion 162 defines a driving feature 165, for example a hexagonally-shaped recess, configured to receive a drive mechanism (not shown) for implanting the fastening member 158 into bone tissue (FIG. 32). In some embodiments, the shaft portion 160 defines a self-drilling feature 166 formed adjacent the self-tapping feature 164 as illustrated in FIGS. 33 and 34.

Figure 35:
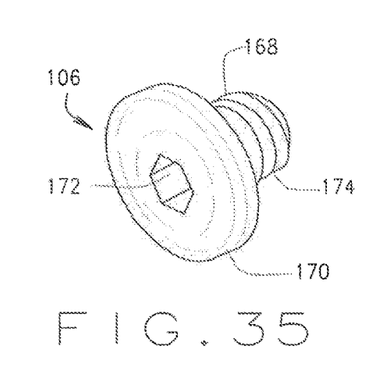
FIG. 35 is a perspective view of a connector used to couple the modular blade component to either the Varus plate component or Valgus plate component.
Figure 36:
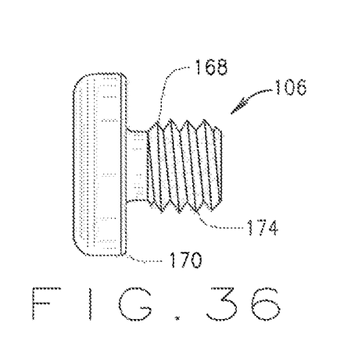
FIG. 36 is a side view of the connector of FIG. 35.

Referring to FIGS. 35 and 36, the connector 106 is used to secure the modular blade component 104 to either the Varus plate component 102 or the Valgus plate component 202. In one embodiment, the connector 106 may include a threaded portion 168 that extends axially from a head portion 170 and defines a plurality of external threads 174 for securing the connector 106 to the second recess 133 and through the recess opening 135 as illustrated in FIG. 20 when the connector 106 is used to secure the modular blade component 104 to the Varus plate connector 102; however, the connector 106 may also be used to similarly secure the modular blade component 104 to the Valgus plate connector 202 as illustrated in FIGS. 22 and 23.

Figure 37:
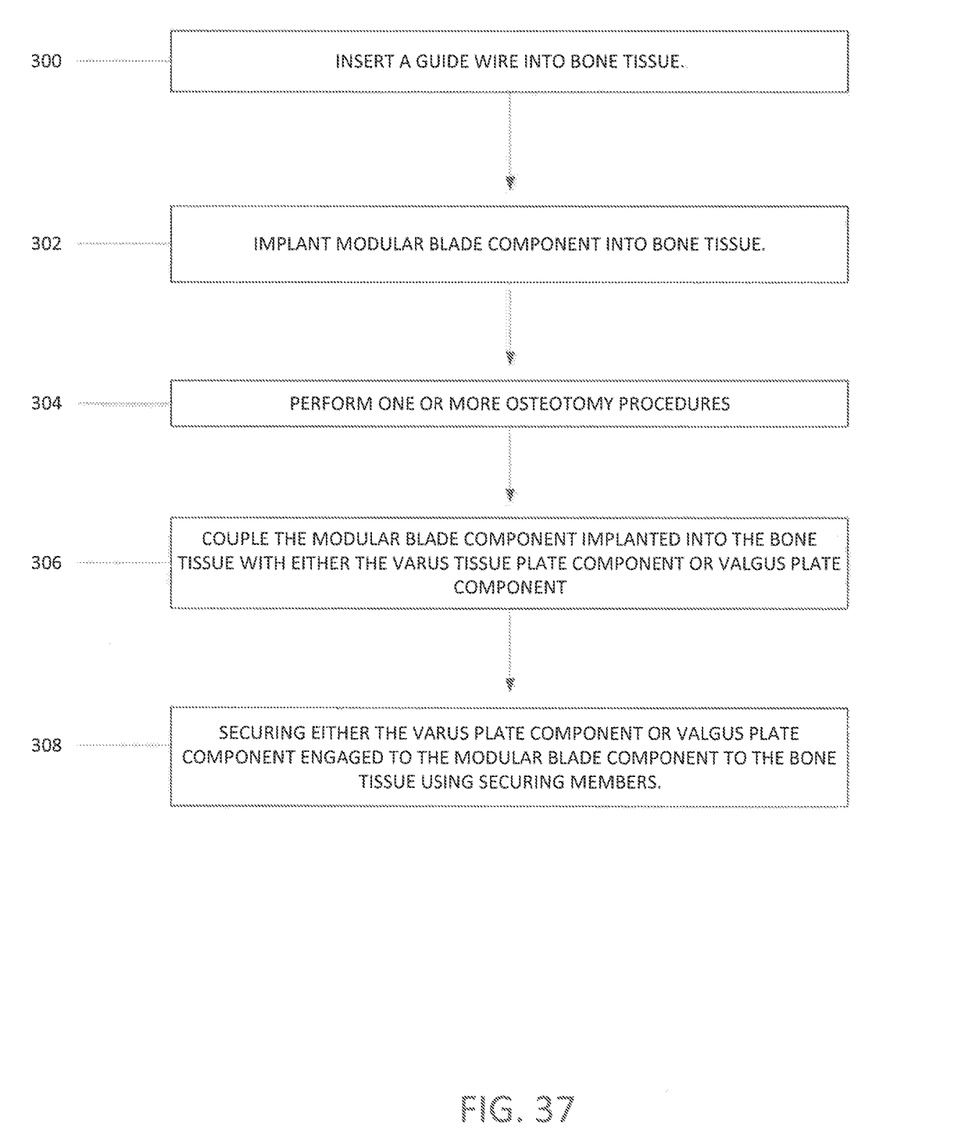
FIG. 37 is a flow chart illustrating one method for implanting the blade-plate assembly.

Referring to FIG. 37, a flow chart illustrates one method for using either the Varus blade-plate assembly 100 or the Valgus blade-plate assembly 200 when performing an osteotomy procedure. At block 300, insert a guide wire into the bone tissue. At block 302, implant the modular blade component 104 into the bone tissue. At block 304, perform one or more osteotomy procedures. At block 306, coupling either the Varus plate component 102 or Valgus plate component 202 to the implanted modular blade component 104. At block 308, secure either the Varus plate component 102 or the Valgus plate component 202 that is engaged to the modular blade component 104 to the bone tissue using a plurality of securing members 158.

It should be understood from the foregoing that, while particular embodiments have been illustrated and described, various modifications can be made thereto without departing from the spirit and scope of the invention as will be apparent to those skilled in the art. Such changes and modifications are within the scope and teachings of this invention as defined in the claims appended hereto.

What is claimed is:

1. An osteotomy blade-plate assembly comprising:
a modular plate component having an anterior surface, a posterior surface and a side surface that collectively define a proximal portion, a distal portion and a transition portion formed between the distal portion and proximal portion, wherein the proximal portion is oriented along a first longitudinal axis and the distal portion is oriented along a second longitudinal axis such that the first longitudinal axis is in parallel relation relative to the second longitudinal axis, and wherein the transition portion is oriented along a third axis that is not parallel relative to the first and second longitudinal axes;
a modular blade component having a support portion configured to be coupled to the plate component and a blade portion extending axially outward from the support portion along a fourth axis that is in perpendicular relation relative to the first and second longitudinal axes, wherein the blade portion defines a channel; and
a connector configured to couple the plate component to the support portion of the modular blade component, wherein the anterior surface of the proximal portion of the plate component defines a first recess configured to receive the support portion of the modular blade component when coupling the modular blade component to the plate component, wherein the first recess defines a first angled mating surface and the support portion defines a second angled mating surface that forms a flush mating engagement with the first angled mating surface that couples the modular plate component to the modular blade component.

2. The osteotomy blade-plate assembly of claim 1, wherein the anterior surface of the distal portion of the plate component defines a curved configuration.

3. The osteotomy blade-plate assembly of claim 1, wherein the first recess is in communication with a clearance hole that communicates with the channel when the modular blade component is coupled to the plate component.

4. The osteotomy blade-plate assembly of claim 1, wherein the first recess communicates with a second recess defined along the posterior surface of the plate component that is configured to receive the connector when coupling the modular blade component to the plate component.

5. The osteotomy blade-plate assembly of claim 1, wherein the distal portion of the plate component defines a plurality of openings each aligned along a fifth axis that is in parallel relation relative to the third axis of the modular blade component.

6. The osteotomy blade-plate assembly of claim 5, wherein at least one of the plurality of openings is aligned along a sixth axis that is not in parallel relation relative to the fifth axis.

7. The osteotomy blade-plate assembly of claim 1, wherein the distal portion of the plate component defines a plurality of openings configured to receive a respective securing member for securing the plate component to bone tissue.

8. The osteotomy blade-plate assembly of claim 4, wherein the distal portion of the plate component defines a plurality of openings each aligned along a fifth axis that is in parallel relation relative to the third axis of the modular blade component.

9. The osteotomy blade-plate assembly of claim 8, wherein at least one of the plurality of openings is aligned along a sixth axis that is not in parallel relation relative to the fifth axis.

10. An osteotomy blade-plate assembly comprising:
a modular plate component having an anterior surface, a posterior surface and a side surface that collectively define a proximal portion, a distal portion and a transition portion formed between the distal portion and proximal portion, wherein the proximal portion is oriented along a first longitudinal axis and the distal portion is oriented along a second longitudinal axis such that the first longitudinal axis is in parallel relation relative to the second longitudinal axis, and wherein the transition portion is oriented along a third axis that is not parallel relative to the first and second longitudinal axes;
a modular blade component having a support portion configured to be coupled to the plate component and a blade portion extending axially outward from the support portion along a fourth axis that is in perpendicular relation relative to the first and second longitudinal axes, wherein the blade portion defines a channel; and
a connector configured to couple the plate component to the support portion of the modular blade component,
wherein the anterior surface of the proximal portion of the plate component defines a first recess configured to receive the support portion of the modular blade component when coupling the modular blade component to the plate component, and
wherein the channel is in direct communication with a first opening defined along the support portion and an opposite second opening defined along a blade tip of the blade portion.

11. An osteotomy blade-plate assembly comprising:
a modular plate component having an anterior surface, a posterior surface and a side surface that collectively define a proximal portion, a distal portion and a transition portion formed between the distal portion and proximal portion, wherein the distal portion is oriented along a first longitudinal axis and the proximal portion is oriented along a second axis such that the first longitudinal axis is not in parallel relation to the second axis, and wherein the transition portion is oriented along a third axis that is in perpendicular relation relative to the second axis of the proximal portion;
a modular blade component having a support portion configured to be coupled to the plate component and a blade portion extending axially outward from the support portion along a fourth axis that is in perpendicular relation relative to the second axis and in parallel relation to the third axis of the transition portion, wherein the blade portion defines a channel; and
a connector configured to couple the plate component to the support portion of the modular blade component.

12. The osteotomy blade-plate assembly of claim 11, wherein the anterior surface of the distal portion of the plate component defines a curved configuration.

13. The osteotomy blade-plate assembly of claim 11, wherein the anterior surface of the proximal portion of the plate component defines a first recess configured to receive the support portion of the modular blade component when coupling the modular blade component to the plate component.

14. The osteotomy blade-plate assembly of claim 13, wherein the first recess is in communication with a clearance hole that communicates with the channel when the modular blade component is coupled to the plate component.

15. The osteotomy blade-plate assembly of claim 13, wherein the first recess communicates with a second recess defined along the posterior surface of the plate component that is configured to receive the connector when coupling the modular blade component to the plate component.

16. The osteotomy blade-plate assembly of claim 13, wherein the channel is in direct communication with a first opening defined along the support portion and an opposite second opening defined along a blade tip of the blade portion.

17. The osteotomy blade-plate assembly of claim 13, wherein the first recess defines a first angled mating surface and the support portion defines a second angled mating surface that forms a flush mating engagement with the first angled mating surface that couples the modular plate component to the modular blade component.

18. The osteotomy blade-plate assembly of claim 11, wherein the distal portion of the plate component defines a plurality of openings configured to receive a respective securing member for securing the plate component to bone tissue.

19. A method for using an osteotomy blade-plate assembly comprising:
inserting a guide wire into bone tissue;
providing a modular blade component comprising:
a support portion and a blade portion, the blade portion extending axially outward from the support portion in perpendicular relation to the support portion, wherein the blade portion defines a channel;
implanting the modular blade component within the bone tissue of an individual;
performing at least one osteotomy to the bone tissue;
providing either a first plate component or a second plate component, the
first plate component comprising:
an anterior surface, a posterior surface and a side surface that collectively define a proximal portion, a distal portion and a transition portion formed between the distal portion and proximal portion, wherein the proximal portion is oriented along a first longitudinal axis and the distal portion is oriented along a second longitudinal axis, and wherein the transition portion is oriented along a third axis that is not parallel relative to the first and second longitudinal axes; and
the second plate component comprising:
an anterior surface, a posterior surface and a side surface that collectively define a proximal portion, a distal portion and a transition portion formed between the distal portion and proximal portion, wherein the distal portion is oriented along a fourth longitudinal axis and the proximal portion is oriented along a fifth axis such that the fourth longitudinal axis is not in parallel relation relative to the fifth axis, and wherein the transition portion is oriented along a sixth axis that is in perpendicular relation relative to the fifth axis of the proximal portion;
coupling the modular blade component implanted within the bone tissue to either the first plate component or the second plate component with a connector, wherein the connector is configured to engage the support portion of the modular blade component to either the first plate component or the second plate component; and securing either the first plate component or the second plate component to the bone tissue using a plurality of securing members.

20. The method of claim 19, wherein the distal portion of the first plate component defines a plurality of openings oriented in parallel relation relative to the blade portion.

21. The method of claim 19, wherein the distal portion of the second plate component defines a plurality of openings, wherein at least one of the plurality of openings is oriented in a parallel relation relative to the blade portion and another one of the plurality of openings is aligned in a non-parallel relation relative to the blade portion.

22. The method of claim 19, wherein the support portion of the modular blade component defines a connector aperture and the first and second plate components each define a recess opening in which the connector aperture is aligned with the recess opening when the modular blade component is coupled to either the first plate component or the second blade component, wherein the connector is configured to be received within the aligned recess.

\* \* \* \* \*